(12) United States Patent
Baker et al.

(10) Patent No.: US 8,053,564 B2
(45) Date of Patent: Nov. 8, 2011

(54) CROSS-LINKED ANTIBODIES

(75) Inventors: Terence Seward Baker, Slough (GB);
Catherine McKay, Slough (GB);
Timothy John Norman, Slough (GB);
John Robert Porter, Slough (GB)

(73) Assignee: UCB Pharma S.A., Brussels (BE)

( * ) Notice: Subject to any disclaimer, the term of this patent is extended or adjusted under 35 U.S.C. 154(b) by 690 days.

(21) Appl. No.: 11/596,654

(22) PCT Filed: May 17, 2005

(86) PCT No.: PCT/GB2005/001950
§ 371 (c)(1),
(2), (4) Date: Dec. 23, 2009

(87) PCT Pub. No.: WO2005/113605
PCT Pub. Date: Dec. 1, 2005

(65) Prior Publication Data
US 2008/0160017 A1    Jul. 3, 2008

(30) Foreign Application Priority Data

May 19, 2004  (GB) .................................. 0411186.0

(51) Int. Cl.
*A61K 39/44* (2006.01)
*C07K 1/10* (2006.01)
*C07K 1/04* (2006.01)

(52) U.S. Cl. ..................... 530/391.1; 530/402; 530/404; 530/405

(58) Field of Classification Search .................. None
See application file for complete search history.

(56) References Cited

U.S. PATENT DOCUMENTS

| 5,262,524 | A | 11/1993 | Anderson et al. |
| 6,177,554 | B1 * | 1/2001 | Woo et al. ................ 536/23.1 |
| 7,105,160 | B1 * | 9/2006 | Smith ........................ 424/179.1 |

FOREIGN PATENT DOCUMENTS

| DE | 3935257 | 4/1991 |
| WO | WO92/22583 | 12/1992 |
| WO | WO99/64460 | 12/1999 |
| WO | WO00/27435 | 5/2000 |
| WO | WO2004/000802 | 12/2003 |
| WO | WO2004/009082 | 1/2004 |

OTHER PUBLICATIONS

Mattson et al. A practical approach to crosslinking. Molecular Biology Reports 1993, vol. 17, pp. 167-183.*
Lemieux G.A. et al., "Chemoselective Ligation Reactions with Proteins, Oligosaccharides and Cells", Trends in Biotechnology Elsevier Publications, vol. 16, No. 12, Dec. 1, 1998, pp. 506-513.
Dhawan Subhash, "Design and Construction of Novel Molecular Conjugates for Signal Amplification (I): Conjugation of Multiple Horseradish Peroxidase Molecules to Immunoglobulin Via Primary Amines on Lysine Peptide Chains", Peptides, vol. 23, No. 12, Dec. 2002, pp. 2091-2098.
International Search Report for PCT/GB2005/001950 dated Jul. 18, 2005.

* cited by examiner

*Primary Examiner* — Shafiqul Haq
(74) *Attorney, Agent, or Firm* — McDonnell Boehnen Hulbert & Berghoff LLP

(57) ABSTRACT

The present invention provides a compound consisting essentially of the following elements: one or more reactive groups; and two or more cross-linked antibodies or fragments thereof; characterised in that the or each reactive group is suitable for attaching an effector molecule but does not react with any of the antibodies or fragments thereof.

4 Claims, 2 Drawing Sheets

CROSS-LINKED ANTIBODIES

Figure 1:
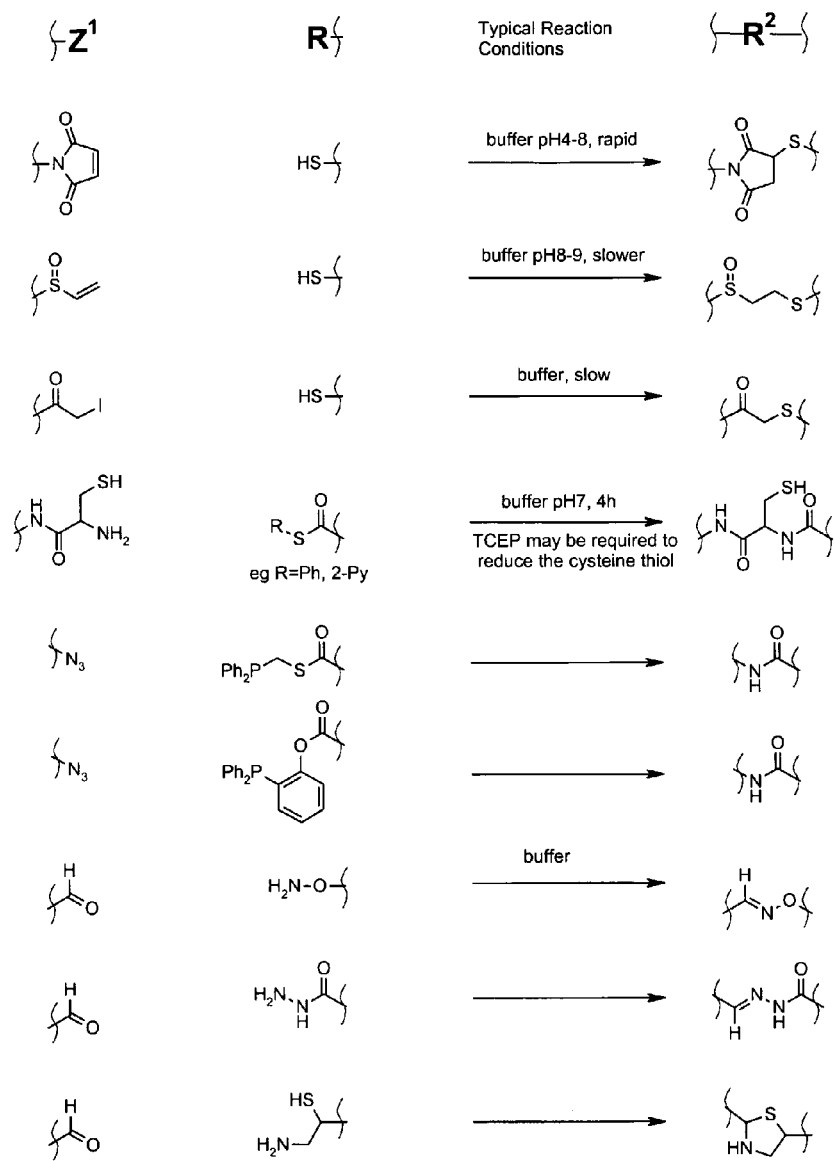
Figure 1:
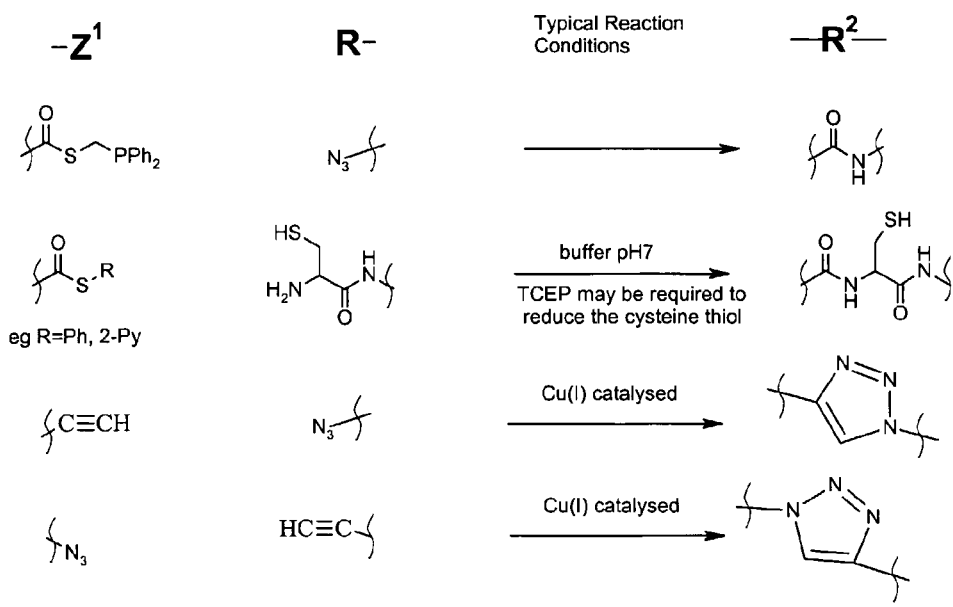

The present invention relates to compounds for use in attaching effector molecules to antibodies. More specifically the invention relates to molecules comprising cross-linked antibodies to which an effector molecule may be attached. Methods for the production of such molecules, and pharmaceutical compositions containing them, are also provided.

The binding specificity of antibodies can be used to deliver effector molecules, such as drugs, to specific therapeutic targets such as tumor cells. Effector molecules may be attached to antibodies using various methods including for example, direct attachment (see for example, U.S. Pat. No. 5,677,425; EP0948544) or attachment via a linker (U.S. Pat. No. 5,218,128).

Cross-linked antibodies are well known in the art (see for example U.S. Pat. No. 5,262,524). Certain cross-linked antibodies have been demonstrated to have improved binding capacities, improved blood clearance in vivo and improved tissue distribution compared to natural immunoglobulins. See for example WO92/22583 which describes tri- and tetravalent monospecific antigen-binding proteins comprising Fab' fragments bound to each other by a connecting structure. WO92/22583 also describes the use of the connecting structure as a site for the attachment of effector molecules.

The present invention provides compounds consisting essentially of the following elements: one or more reactive groups; and two or more cross-linked antibodies or fragments thereof; characterised in that the or each reactive group is suitable for attaching an effector molecule but does not react with any of the antibodies or fragments thereof.

The present invention therefore provides novel linkers for cross-linking antibodies to which effector molecules may be attached. Advantageously, the linker molecules comprise a single reactive group which is suitable for site-specific attachment of an effector molecule but which does not react with the antibodies attached to the linker. In addition the reactive group is distal from the antigen binding sites. These features allow effector molecules to be attached to the cross-linked antibodies without disrupting the antigen binding capacity of the antibodies. In addition, the compounds of the present invention are more efficient to prepare and versatile to use than prior art compounds. By attaching the effector molecules to the preformed cross-linked antibodies rather than the reverse (first attaching a linker to an effector molecule and then attaching the antibodies) unwanted side reactions are minimised creating a more uniform product. Furthermore, as the cross-linked antibodies are prepared in the absence of the effector molecule, less stable effector molecules can be selected for subsequent attachment. A stock of preformed cross-linked antibody also allows a virtually limitless range of effector molecules to be attached without the need to synthesise the entire compound ab initio each time a different compound is required.

Preferably the compounds of the present invention comprise one or two reactive groups, more preferably one reactive group.

The present invention therefore also provides compounds consisting essentially of the following elements: a reactive group; and two or more cross-linked antibodies or fragments thereof; characterised in that the reactive group is suitable for attaching an effector molecule but does not react with any of the antibodies or fragments thereof.

Particular examples of the present invention are provided in formula (I) or (II):

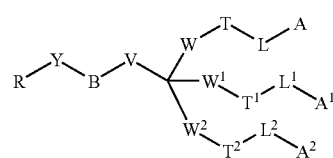

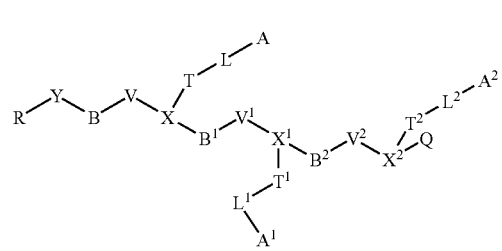

wherein:

A, $A^1$ and $A^2$ independently represent the residue of an antibody or fragment thereof;

L, $L^1$ and $L^2$ independently represent a spacer group;

R represents a reactive group which is suitable for attaching an effector molecule but does not react with any of A, $A^1$ and $A^2$;

Y represents a covalent bond or $-(CH_2)_y-$;

B, $B^1$ and $B^2$ independently represent $-CONH-$, $-NHCO-$ or $-CO-$;

V, $V^1$ and $V^2$ independently represent a covalent bond or $-(CH_2)_v-$;

X, $X^1$ and $X^2$ independently represent $CR^1$ or N;

W, $W^1$ and $W^2$ independently represent $-(CH_2)_wO-$;

T, $T^1$ and $T^2$ independently represent a linker group;

Q represents $CO_2R^a$ or $CONR^aR^b$;

$R^a$ represents hydrogen or $C_{1-4}$ alkyl;

$R^b$ represents hydrogen or $C_{1-4}$ alkyl;

$R^1$ represents hydrogen or $C_{1-4}$ alkyl;

v is 1, 2, 3 or 4;

w is 1, 2, 3 or 4; and y is 1, 2, 3, 4, 5 or 6.

Also provided by the present invention are cross-linked antibodies to which an effector molecule is attached. Particular examples of this aspect of the invention are provided in formula (III) and (IV):

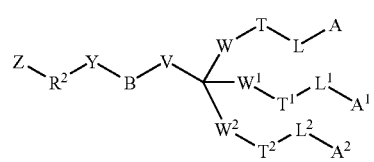

-continued

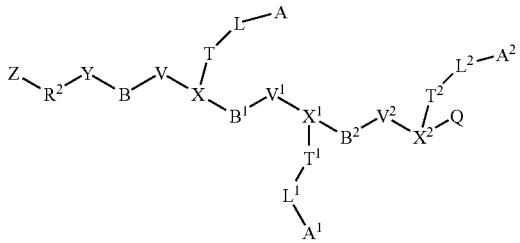

(IV)

wherein

Z is the residue of an effector molecule;

R² is the functional group resulting from the attachment of Z; and each of the other variables is as defined above in relation to formula (I) or (II).

As used herein, the term "$C_{1-4}$ alkyl" refers to straight-chained and branched alkyl groups containing 1 to 4 carbon atoms. Such groups are methyl, ethyl, n-propyl, isopropyl, n-butyl, isobutyl, sec-butyl and tert-butyl.

As used herein, the term "residue" will be understood to mean that portion of an effector molecule or an antibody or fragment thereof which remains after it has undergone a substitution reaction as such terminology is familiar to the person skilled in the art.

The residues A, A¹ and A² include residues of whole antibodies and functionally active fragments or derivatives thereof and may be, but are not limited to, polyclonal, monoclonal, humanized or chimeric antibodies, single chain antibodies, Fab fragments, Fab' and F(ab')₂ fragments and epitope-binding fragments of any of the above.

Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD or IgA) or subclass of immunoglobulin molecule.

Monoclonal antibodies may be prepared by any method known in the art such as the hybridoma technique (Kohler & Milstein, Nature, 1975, 256, 495-497), the trioma technique, the human B-cell hybridoma technique (Kozbor et al., Immunology Today, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., Proc. Natl. Acad. Sci. USA, 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule (see, for example, U.S. Pat. No. 5,585,089).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic.

The antibodies for use in the present invention can also be generated using various phage display methods known in the art and include those disclosed by Brinkman et al., J. Immunol. Methods, 1995, 182, 41-50; Ames et al., J. Immunol. Methods, 1995, 184, 177-186; Kettleborough et al. Eur. J. Immunol., 1994, 24, 952-958; Persic et al., Gene, 1997 187, 9-18; and Burton et al., Advances in Immunology, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580, 717; 5,427,908; 5,750,753; 5,821,047; 5,571,698; 5,427,908; 5,516,637; 5,780,225; 5,658,727; 5,733,743; and 5,969, 108.Techniques for the production of single chain antibodies, such as those described in U.S. Pat. No. 4,946,778, can also be adapted to produce single chain antibodies. Also, transgenic mice, or other organisms, including other mammals, may be used to express humanized antibodies.

In one example the antibody fragments are Fab' fragments which possess a native or a modified hinge region. A number of modified hinge regions have already been described, for example, in U.S. Pat. No. 5,677,425, WO9915549, and WO9825971 and these are incorporated herein by reference Particular antibody fragments include those described in WO2005003169, WO2005003170 and WO2005003171.

Preferably the antibody fragments for use in the present invention contain a single free thiol, preferably in the hinge region.

The term 'cross-linked antibodies' as used herein refers to two, three or four antibodies or fragments thereof, linked by a connecting structure. The connecting structure may be any molecular structure capable of linking the antibodies or fragments thereof together such as those described herein. Preferably the cross-linked antibody portion of the molecules according to the present invention comprises three antibody fragments, preferably Fab' fragments.

Each of the antibodies or fragments thereof in the cross-linked antibody portion of the molecules of the present invention will in general be capable of selectively binding to an antigen. Each antibody may bind the same or a different antigen. Hence the cross-linked antibody portion of the molecules according to the present invention may be monospecific, bispecific, trispecific or tetraspecific. Preferably the cross-linked antibody portion of the molecules according to of the present invention is monospecific.

The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, CD70, CD134, carcinoembryonic antigen (CEA), MUC-1, MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

Suitably, A, A$^1$ and A$^2$ are identical.

The spacer groups for use in the present invention, will suitably comprise any moiety familiar to the person skilled in the art which is capable of forming a bridge between the linker and the antibody or fragment thereof. In particular the spacer groups L, L$^1$ and L$^2$ will suitably comprise any moiety familiar to the person skilled in the art which is capable of forming a bridge between the linker T, T$^1$ and T$^2$ and the residue A, A$^1$ and A$^2$ respectively. In one example, where A, A$^1$ or A$^2$ is the residue of an antibody or a fragment thereof containing a cysteine residue the corresponding spacer group L, L$^1$ or L$^2$ will suitably be succinimide (i.e. the reaction product of a maleimide residue with the cysteine-containing polypeptide residue A, A$^1$ or A$^2$ via a thiol linkage and the linker T, T$^1$ or T$^2$ through the maleimide nitrogen atom).

Suitably, L, L$^1$ and L$^2$ are identical.

The linker groups T, T$^1$ and T$^2$ will suitably comprise any moiety familiar to the person skilled in the art which is capable of forming a bridge between the spacer group L, L$^1$ and L$^2$ and the oxygen atom of W, W$^1$ and W$^2$ respectively, or X, X$^1$ and X$^2$ respectively.

Typical examples of T, T$^1$ and T$^2$ include —(CH$_2$)$_t$-, —(CH$_2$)$_t$NHCO(CH$_2$)$_n$-, —(CH$_2$)$_t$NHCO(CH$_2$)$_x$NHCO(CH$_2$)$_n$-, —(CH$_2$)$_t$NHCO(CH$_2$)$_p$(OCH$_2$CH$_2$)$_z$NHCO(CH$_2$)$_n$-, —(CH$_2$)$_t$NHCO(CH$_2$)$_m$-,

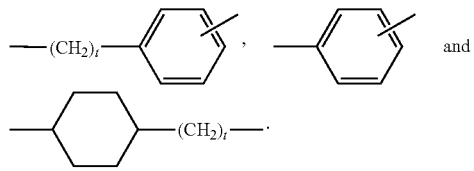

wherein
t is 1, 2, 3, 4, 5, 6, 7, 8, 9 or 10;
n is 1, 2, 3, 4, 5 or 6;
x is 2, 3, 4, 5 or 6;
z is 1 to 500;
p is 1, 2, 3, 4, 5 or 6;
m is 1, 2, 3, 4, 5, or 6; and
r is 2, 3, 4 or 5.

In one embodiment, T represents —(CH$_2$)$_t$-.
In another embodiment, T represents —(CH$_2$)$_t$NHCO(CH$_2$)$_n$-.
In another embodiment, T represents —(CH$_2$)$_t$NHCO(CH$_2$)$_x$NHCO(CH$_2$)$_n$-.
In another embodiment, T represents —(CH$_2$)$_t$NHCO(CH$_2$)$_p$(OCH$_2$CH$_2$)$_z$NHCO(CH$_2$)$_n$-.
In another embodiment, T represents —(CH$_2$)$_r$NHCO(CH$_2$)$_m$-.
In one embodiment, T$^1$ represents —(CH$_2$)$_t$-.
In another embodiment, T$^1$ represents —(CH$_2$)$_t$NHCO(CH$_2$)$_n$-.
In another embodiment, T$^1$ represents —(CH$_2$)$_t$NHCO(CH$_2$)$_x$NHCO(CH$_2$)$_n$-.
In another embodiment, T$^1$ represents —(CH$_2$)$_t$NHCO(CH$_2$)$_p$(OCH$_2$CH$_2$)$_z$NHCO(CH$_2$)$_n$-.
In another embodiment, T$^1$ represents —(CH$_2$)$_r$NHCO(CH$_2$)$_m$-.
In one embodiment, T$^2$ represents —(CH$_2$)$_t$-.
In another embodiment, T$^2$ represents —(CH$_2$)$_t$NHCO(CH$_2$)$_n$-.
In another embodiment, T$^2$ represents —(CH$_2$)$_t$NHCO(CH$_2$)$_x$NHCO(CH$_2$)$_n$-.

In another embodiment, T represents —(CH$_2$)$_t$NHCO(CH$_2$)$_p$(OCH$_2$CH$_2$)$_z$NHCO(CH$_2$)$_n$-.
In another embodiment, T$^2$ represents —(CH$_2$)$_r$NHCO(CH$_2$)$_m$-.

Suitably T, T$^1$ and T$^2$ are identical.
In one embodiment, X represents CR$^1$. In another embodiment, X represents N.
In one embodiment, X$^1$ represents CR$^1$. In another embodiment, X$^1$ represents N.
In one embodiment, X$^2$ represents CR$^1$. In another embodiment, X$^2$ represents N.
Suitably X, X$^1$ and X$^2$ are identical.
In one embodiment, B represents —CONH—. In another embodiment, B represents —NHCO—. Where B represents —CONH—, X typically represents CH.
In one embodiment, B$^1$ represents —CONH—. In another embodiment, B$^1$ represents —NHCO—. Where B$^1$ represents —CONH—, X$^1$ typically represents CH.
In one embodiment, B represents —CONH—. In another embodiment, B$^2$ represents —NHCO—. Where B represents —CONH—, X$^2$ typically represents CH.
Suitably B, B$^1$ and B$^2$ are identical.
In a preferred embodiment, V represents a covalent bond. In another embodiment, V represents —(CH$_2$)$_v$- in which v is as defined above.
In a preferred embodiment, V$^1$ represents a covalent bond. In another embodiment, V$^1$ represents —(CH$_2$)$_v$- in which v is as defined above.
In a preferred embodiment, V$^2$ represents a covalent bond. In another embodiment, V$^2$ represents —(CH$_2$)$_v$- in which v is as defined above.
Suitably, V, V$^1$ and V$^2$ are identical.
In a preferred embodiment, R$^a$ is hydrogen. In another embodiment, R$^a$ represents C$_{1-4}$alkyl, especially methyl.
In a preferred embodiment, R$^b$ is hydrogen. In another embodiment, R$^b$ represents C$_{1-4}$alkyl, especially methyl.
In one embodiment Q is CO$_2$H. In another embodiment Q is CONH$_2$.
In a preferred embodiment, R$^1$ is hydrogen. In another embodiment, R$^1$ represents C$_{1-4}$alkyl, especially methyl.
In one embodiment y is 1.
In another embodiment y is 2.
In one embodiment t is 2. In another embodiment, t is 3. In an additional embodiment, t is 4. Favourably, t is 3.
In one embodiment r is 4.
In one embodiment m is 5.
In one embodiment n is 2.
Typically, z may be in the range 1 to 10; or in the range 10 to 25; or in the range 25 to 50; or in the range 50 to 100; or in the range 100 to 250; or in the range 250 to 500. Specific values of z include 1, 2, 3, 4, 5, 6, 10, 25, 50, 100, 250 and 500.
In one embodiment z is 4.
In one embodiment x is 5.
In one embodiment p is 2.

The residue Z in the compounds of formulas (III) and (IV) above will suitably be a residue of an effector molecule. It will be appreciated that the effector molecule may comprise a single effector molecule or two or more such molecules so linked as to form a single moiety that can be attached to the compounds of the present invention as a single residue, Z. Examples of such moieties include effector molecules linked by branched connecting structures. Effector molecules for use in the present invention include biologically active compounds suitable for medicinal or diagnostic use in the treatment of animals, including humans.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules may include proteins or polymers that may be used to extend the half-life and/or decrease the immunogenicity of the compound of the present invention. Examples of suitable proteins include albumin and albumin binding proteins. Examples of suitable polymers include any synthetic or naturally occurring substantially water-soluble, substantially non-antigenic polymer including, for example, optionally substituted straight or branched chain polyalkylene, polyalkenylene, or polyoxyalkylene polymers or branched or unbranched polysaccharides, e.g. a homo- or hetero-polysaccharide such as lactose, amylose, dextran or glycogen. Particular optional substituents which may be present on the above-mentioned synthetic polymers include one or more hydroxy, methyl or methoxy groups. Particular examples of synthetic polymers include optionally substituted straight or branched chain poly(ethyleneglycol), poly (propyleneglycol), poly(vinylalcohol) or derivatives thereof, especially optionally substituted poly(ethyleneglycol) such as methoxypoly(ethyleneglycol).

Preferably the polymer for use in the present invention is a polyalkylene oxide such as polyethylene glycol (PEG). As regards attaching PEG moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C.; and "Bioconjugation Protein Coupling Techniques for the Biomedical Sciences", 1998, M. Aslam and A. Dent, Grove Publishers, New York.

The size of the polymer may be varied as desired, but will generally be in an average molecular weight range from 250 to 100,000 Da, preferably from 5,000 to 50,000 Da, more preferably from 10,000 to 40,000 Da and still more preferably from 20,000 to 40,000 Da. Polymer size may in particular be selected on the basis of the intended use of the product, for example ability to localize to certain tissues such as tumors or extend circulating half-life (for review see Chapman, 2002, Advanced Drug Delivery Reviews, 54, 531-545).

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, $\alpha$-interferon, $\beta$-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

The reactive group R for use in the present invention is any group suitable for attaching an effector molecule but which does not react with any of the antibodies or fragments thereof attached to the linker. Typically R is a group that will react with a residue, Z, but will not react with any of the antibodies or fragments thereof attached to the linker. Such groups are well known in the art and may include thiols, thioesters, oxyamines and hydrazides.

In one embodiment R is a thiol group —SH, in which case $R^2$ will be the divalent thiol residue —S—. In another embodiment R is a thioester moiety, e.g. a group of formula —C(O)SR$^{10}$ where R$^{10}$ represents an aryl or heteroaryl group e.g. phenyl or pyridinyl. In another embodiment R is the oxyamine group —ONH$_2$. In another embodiment R is a hydrazide group —CONHNH$_2$.

It will be appreciated by persons skilled in the art that R will be selected to react with a particular reactive group $Z^1$ present on Z. Preferably the reactive group $Z^1$ will be selected such that it does not react with the antibodies or fragments thereof attached to the linker. In addition, the reactive group $Z^1$ and the reactive group R will be selected such that the reaction between them can take place under mild conditions that will not affect the biological activity of the antibodies or fragments thereof or the effector molecule.

$R^2$ is the divalent functional group resulting from the attachment of Z to R.

Suitable groups are well known in the art and some examples of possible R and $Z^1$ groups and of the resulting divalent functional groups ($R^2$) are provided in FIG. 1.

Other examples of groups suitable for use as reactive groups $Z^1$ and R include groups used in linking reactions such as Click Chemistry (Kolb and Sharpless, 2003, DDT, 8, 1128-1137), Staudinger ligations (Wang et al., 2003, Bioconjugate Chemistry, 14, 697-701) and Traceless Staudinger ligations (Nilsson et al., 2001, Organic Letters, 3, 9-12; Saxon et al., 2000, 2, 2141-2143).

Also provided by the present invention are compounds consisting essentially of the following elements: one or more reactive groups as defined herein or a protected derivative thereof; and a linker suitable for cross-linking two or more antibodies or fragments thereof; characterised in that the or each reactive group is suitable for attaching an effector molecule and it or its protected derivative thereof does not react with the antibodies or fragments thereof or the spacer group on the linker to which they will be attached.

Preferably the compounds according to this aspect of the present invention comprise one or two reactive groups, more preferably one reactive group.

The present invention therefore also provides compounds consisting essentially of the following elements: a reactive group as defined herein or a protected derivative thereof; and a linker suitable for cross-linking two or more antibodies or fragments thereof; characterised in that the reactive group is suitable for attaching an effector molecule and it or its protected derivative thereof does not react with the antibodies or fragments thereof or the spacer group on the linker to which they will be attached.

Hence, in another aspect, the present invention provides novel compounds which are valuable intermediates for the attachment of antibodies or fragments thereof of which A, $A^1$ and $A^2$ are residues. Thus, the invention also provides compounds of formula (V) and (VI):

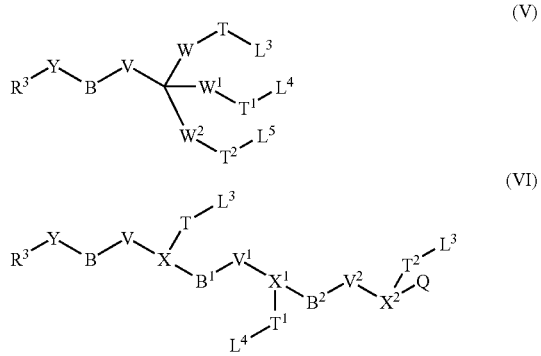

wherein $L^3$, $L^4$ and $L^5$ represent groups capable of attaching the residue A, $A^1$ and $A^2$ respectively, or capable of being converted into such groups;

$R^3$ corresponds to the group R as defined above or represents a protected derivative thereof which does not react with $L^3$, $L^4$ and $L^5$; and each of the other variables is as defined above in relation to formula (I) or (II).

Where $R^3$ is a protected derivative of R, the reactive group R is masked by another group, a 'protecting group' to prevent R from reacting with the spacer groups $L^3$, $L^4$ or $L^5$. Such protected derivatives are capable of being readily converted in the presence of antibodies to the reactive group R. Examples of such groups are protected thiols where the protecting group can be readily removed to provide a free thiol for reaction with Z. Conditions for removal are preferably such that the biological activity of the antibodies or fragments thereof is not affected. Suitable thiol protecting groups are known in the art and include thiol esters, disulphides, acetyl groups, and propionyl groups.

The groups $L^3$, $L^4$ or $L^5$ may be attached to the corresponding residues A, $A^1$ or $A^2$ through any available amino acid side-chain or terminal amino acid functional group located in the antibody or fragment thereof, for example any free amino, imino, thiol, hydroxy or carboxyl group. Such amino acids may occur naturally in, for example, the antibody fragment or may be engineered into the antibody or fragment thereof using recombinant DNA methods (see, for example, U.S. Pat. No. 5,219,996 and U.S. Pat. No. 5,677,425). In a preferred aspect of the invention the two groups are covalently linked through a thiol group of a cysteine residue located in the antibody or fragment thereof, preferably in the hinge. The covalent linkage will generally be a disulphide bond or a sulphur-carbon bond, preferably the latter. In one example where a thiol group is used as the point of attachment appropriately activated groups, for example thiol-selective derivatives such as maleimide and cysteine derivatives, may be used.

In a preferred feature, the groups $L^3$, $L^4$ and $L^5$ are identical and represent maleimide derivatives attached to the remainder of the molecule through the maleimide nitrogen atom. In another feature, $R^3$ represents an acetyl-protected thiol group. Accordingly, one illustrative subset of the compounds of formula (V) and (VI) above is represented by the compounds of formula (VII) and (VIII):

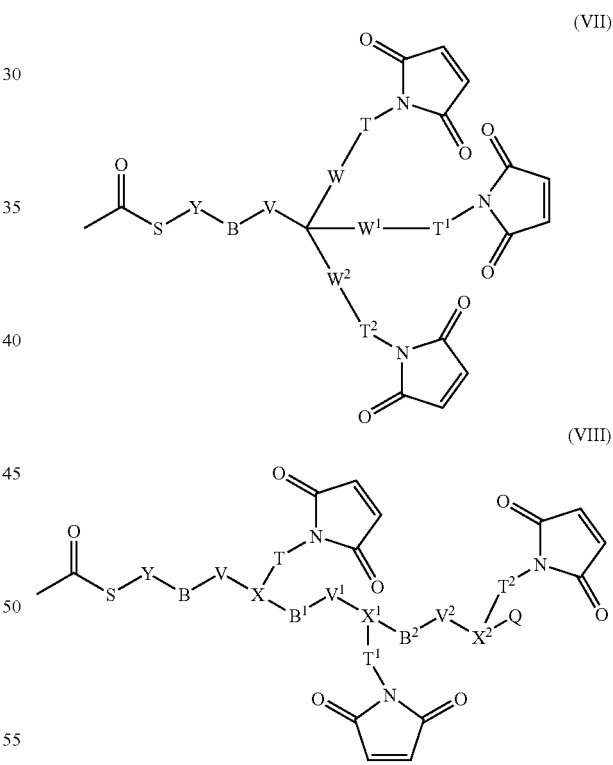

wherein each of the variables is as defined above.

According to a further aspect of the invention there is provided a pharmaceutical composition which comprises a compound of formula (III) or (IV) in association with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (III) and (IV) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (III) and (IV) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of the present invention may be prepared by using methods analogous to those in the Examples provided herein.

Typically the compounds of formula (III) and (IV) may be prepared by a process which comprises attachment of residue Z to a compound of formula (I) or (II) respectively using procedures which are well known to the person skilled in the art.

The compounds of formula (I) and (II) wherein R is a thiol group —SH may be prepared from the corresponding compound of formula (VII) or (VIII) respectively wherein $R^3$ is an acetyl-protected thiol group —SCOCH$_3$ by conventional deprotection methodology, e.g. by incubation in EDTA-containing buffer with hydroxylamine hydrochloride.

The compounds of formula (VII) wherein T, $T^1$ and $T^2$ are each —(CH$_2$)$_t$- may be prepared by reacting a compound of formula (IX):

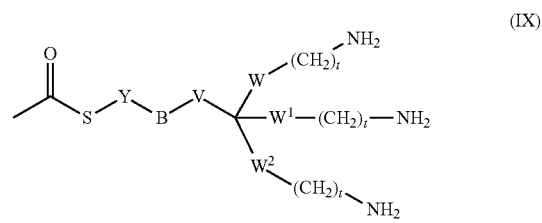

wherein each of the variables is as defined above; with N-methoxycarbonyl maleimide.

The reaction is conveniently effected under basic conditions, e.g. in the presence of aqueous sodium carbonate.

The compounds of formula (VII) wherein T, $T^1$ and $T^2$ are each —(CH$_2$)$_t$NHCO(CH$_2$)$_n$- may be prepared by reacting a compound of formula (IX) as defined above with a compound of formula (X):

(X)

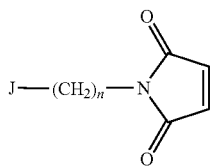

wherein n is as defined above, and J represents an activated carboxylate moiety.

Examples of activated carboxylate moieties for the substituent J include acid chlorides; acid anhydrides; and the ester formed when a carboxylic acid (J=—CO$_2$H) is reacted with N-hydroxysuccinimide or a sulfosuccinimide analogue thereof.

The reaction between compounds (IX) and (X) is conveniently effected in a suitable solvent, e.g. N,N-dimethylformamide, typically in the presence of an organic base, e.g. triethylamine.

The compounds of formula (VII) wherein T, T$^1$ and T$^2$ are each —(CH$_2$)$_t$NHCO(CH$_2$)$_x$NHCO(CH$_2$)$_n$- may be prepared by reacting a compound of formula (IX) as defined above with a compound of formula (XI):

(XI)

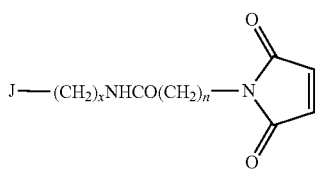

where x, n and J are as defined above; under conditions analogous to those described above for the reaction between compounds (IX) and (X).

The compounds of formula (VII) wherein T, T$^1$ and T$^2$ are each —(CH$_2$)$_t$NHCO(CH$_2$)$_p$(OCH$_2$CH$_2$)$_z$NHCO(CH$_2$)$_n$- may be prepared by reacting a compound of formula (IX) as defined above with a compound of formula (XII):

(XII)

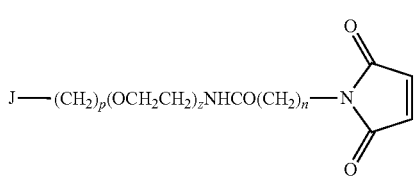

wherein p, z, n and J are as defined above; under conditions analogous to those described above for the reaction between compounds (IX) and (X).

The compounds of formula (VIII) wherein T, T$^1$ and T$^2$ are each —(CH$_2$)$_r$NHCO(CH$_2$)$_m$- may be prepared by reacting a compound of formula (XIII) with a compound of formula (XIV):

(XIII)

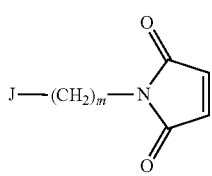

(XIV)

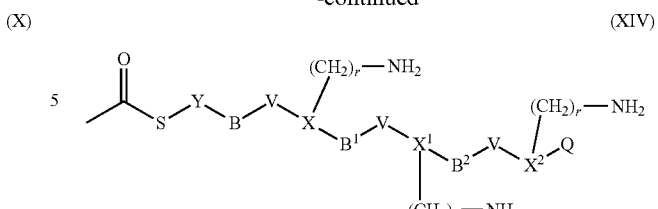

wherein each of the variables is as defined above.

The reaction is conveniently effected under basic conditions, e.g. diisopropylethylamine in dimethylsulfoxide.

Where they are not commercially available, the compounds of formula (IX), (X), (XI), (XII), (XIII) and (XIV) may be prepared by methods analogous to those described in the accompanying Examples, or by standard methods well known from the art.

Where a mixture of products is obtained from any of the processes described above for the preparation of compounds according to the invention, the desired product can be separated therefrom at an appropriate stage by conventional methods such as gel permeation chromatography; cation or anion exchange; preparative HPLC; or column chromatography utilising, for example, silica and/or alumina in conjunction with an appropriate solvent system.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following non-limiting Examples illustrate the invention.

Intermediate 1

3-[2-Amino-3-(2-cyanoethoxy)-2-(2-cyanoethoxymethyl)-propoxy]-propionitrile

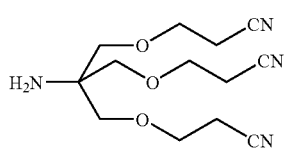

Tris(hydroxymethyl)aminomethane (24.2 g, 0.2 mol) was added to a mixture of dioxane (25 ml) and aqueous potassium hydroxide (1.2 g KOH in 3 ml water). Acrylonitrile (40 ml, 0.61 mol) was added dropwise. After 2 h the solution was stood in a cold water bath to moderate any exothermic reaction and stirred for 16 h at RT. The solution was neutralized with dil. HCl and filtered. The oil was dissolved in DCE, dried (MgSO$_4$), filtered and concentrated. The brown oil was purified by chromatography (SiO$_2$, CH$_2$Cl$_2$/MeOH 1% to 4%) to give the title product (26.9 g, 0.096 mol, 48%) as a colourless oil. $\delta_H$ (400 MHz, CDCl$_3$) 3.71 (6H, t, J 6.0), 3.47 (6H, s), 2.63 (6H, t, J 6.0); TLC (CH$_2$Cl$_2$/MeOH 10%) 0.55.

Intermediate 2

Benzyl {2-(2-cyanoethoxy)-1,1-bis[(2-cyanoethoxy)methyl]ethyl}carbamate

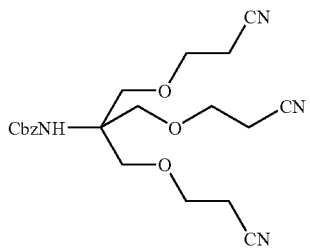

Benzyl chloroformate (5 ml, 35.0 mmol) and saturated aqueous NaHCO$_3$ (150 ml) were added to a solution of product of intermediate 1 (10 g, 35.7 mmol) in dichloromethane (150 ml) under nitrogen. The resulting mixture was stirred for 16 h at RT. The layers were separated. The organic layer was washed with dilute aqueous HCl and water, dried (MgSO$_4$), filtered and concentrated. The crude material was purified by column chromatography (SiO$_2$, EtOAc/hexane 1:4 then 1:2) to give the title product (1.88 g, 7.66 mmol, 57%) as a white solid. $\delta_H$ (400 MHz, CDCl$_3$) 2.67 (6H, t, J 6.0), 3.77 (6H, t, J 6.0), 3.89 (6H, s), 5.16 (2H, s), 5.22 (1H, br.s), 7.43 (5H, m); LCMS (ESI+) 415 (M+H)$^+$, ret time 3.17 mins.

Intermediate 3

Benzyl [2-{3-[(tert-butoxycarbonyl(amino]propoxy-1,1-bis({3-[(tert-butoxycarbonyl)amino]propoxy}methyl)ethyl]carbamate

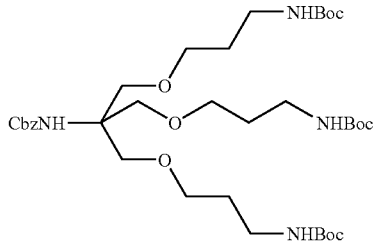

BH$_3$.THF (1.0M in THF, 40 ml, 39.78 mmol) was added slowly at 0° C. to a solution of product of intermediate 2 (5 g, 12.05 mmol) in anhydrous THF (40 ml) under nitrogen. The resulting mixture was stirred for 30 min at 0° C. and 5 h at RT. BH$_3$.THF (1.0M in THF, 8 ml, 8 mmol) and THF (10 ml) were again added and the solution stirred for 16 h at RT. The mixture was poured onto a mixture of ice and dilute HCl (2M) until fizzing stops, and concentrated to dryness. Dichloromethane (80 ml), NEt$_3$ (17 ml, 120.5 mmol) and Boc$_2$O (13.15 g, 60.25 mmol) were added in turn. The resulting mixture was stirred for 16 h at RT, washed with water and brine, dried (MgSO$_4$), filtered and concentrated. The crude material was purified by column chromatography (SiO$_2$, EtOAc/hexane 1:3 then 1:2) to give the title product (1.71 g, 2.35 mmol, 20%) as a colourless, sticky oil. $\delta_H$ (400 MHz, CDCl$_3$) 1.35 (27H, s), 1.64 (6H, quintet, J 6.1), 3.10 (6H, t, J 6.1), 3.41 (6H, t, J 6.1), 3.58 (6H, s), 4.81 (3H, br. m), 4.98 (2H, s), 5.24 (1H, br. m), 7.24 (5H, m); TLC (EtOAc/hexane 1:1) rf 0.37.

Intermediate 4 tert-Butyl [6-amino-6-({3-[(tert-butoxycarbonyl)amino]propoxy}methyl)-15,15-dimethyl-13-oxo-4,8,14-trioxa-12-azahexadec-1-yl]carbamate

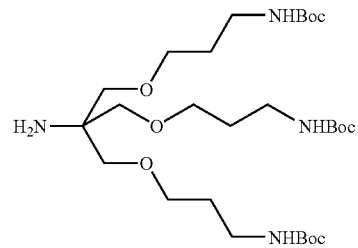

The product of intermediate 3 (1.77 g, 2.43 mmol) was dissolved in ethanol (20 ml) and the flask was submitted to three vacuum/nitrogen cycles. Palladium on charcoal (10%/C, 259 mg, 0.24 mmol) was added. The flask was submitted to three vacuum/hydrogen cycles. The reaction mixture was stirred under a light pressure of hydrogen for 16 h at RT and filtered through a pad a celite. The filtrate was concentrated. The crude oil was purified by column chromatography (SiO$_2$, EtOAc) to give the title product (1.08 g, 1.82 mmol, 75%) as a sticky, yellow oil. $\delta_H$ (400 MHz, CDCl$_3$) 1.36 (27H, s), 1.68 (6H, t, J 5.8), 3.15 (6H, br. S), 3.41-3.39 (12H, m), 4.96 (3H, br. s); TLC (EtOAc/MeOH 20%) rf 0.29; LCMS (ESI+) 593 M$^+$, ret time 2.73 mins.

Intermediate 5

S-[5,5-bis({3-tert-Butoxycarbonyl)amino]propoxy}methyl)-14,14-dimethyl-3,12-dioxo-7,13-dioxa-4,11-diazapentadec-1-yl]ethanethioate

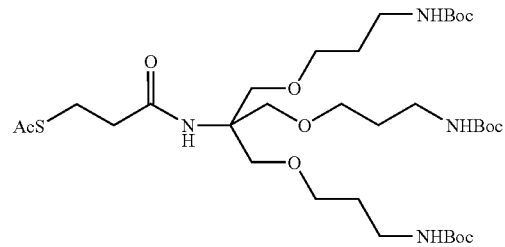

The product of intermediate 4 (469 mg, 1.91 mmol) and NEt$_3$ (0.4 ml, 2.92 mmol) were added to a solution of 3-(acetylthio)propionic acid NHS ester (1.08 g, 1.82 mmol) in dichloromethane (5 ml). The resulting mixture was stirred for 24 h at RT. Product XX (469 mg, 1.91 mmol) and NEt$_3$ (0.8 ml, 5.84 mmol) were again added and the mixture stirred for 24 h at RT. The solution was washed with water and brine, dried (MgSO$_4$), filtered and concentrated. The crude solid was purified by column chromatography (SiO$_2$, EtOAc/hexane 1:4 to 1:1) to give the title product (910 mg, 1.26 mmol, 69%) as a colourless foam. $\delta_H$ (400 MHz, CDCl$_3$) 1.23 (27H, s), 1.52

(6H, t, J 5.9), 2.10 (3H, s), 2.34 (2H, t, J 6.9), 2.91 (2H, t, J 7 Hz), 3.00 (6H, t, J 6.0), 3.28 (6H, t, J 5.6), 3.49 (6H, s), 4.67 (3H, br. s); TLC (EtOAc/hexane 1:1) rf 0.21; LCMS (ESI+) 723 M+, 623 (M-Boc+H)+, ret time 4.15 mins.

Intermediate 6

S-[3-({2-(3-Aminopropoxy)-1,1-bis[(3-aminopropoxy)methyl]ethyl}amino)-3-oxopropyl]ethanethioate (TFA Salt)

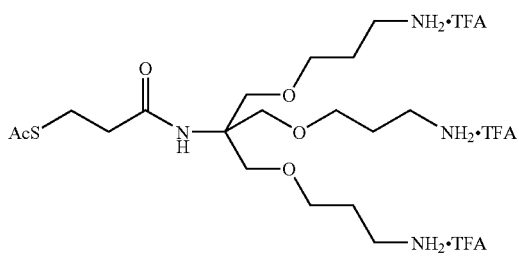

Trifluoroacetic acid (8 ml) was slowly added to a solution of the product of intermediate 5 (900 mg, 1.24 mmol) in dichloromethane (8 ml). The resulting mixture was stirred for 6 h at RT and concentrated. The crude oily material was taken onto the next reaction. $\delta_H$ (400 MHz, CD$_3$OD) 1.91-1.96 (6H, m), 2.33 (3H, s), 2.52 (2H, t, J 6.29), 3.04-3.11 (8H, m), 3.33 (3H, br. s), 3.59 (6H, m), 3.72 (6H, br. s), 4.00 (1H, br. s).

Intermediate 7

3-(2,5-dioxo-2,5-dihydro-1H-pyrrol-1-yl)-N-{6-[(2,5-dioxopyrrolidin-1-yl)oxy]-6-oxohexyl}propanamide

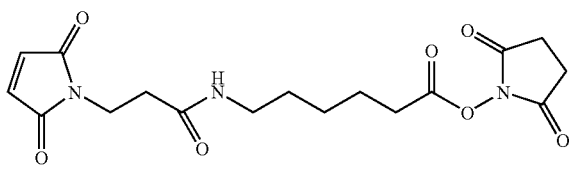

N-Maleimidopropionic acid NHS ester (500 mg, 1.88 mmol) and 6-aminohexanoic acid (235 mg, 1.79 mmol) were dissolved in DCM (200 ml) and stirred for 16 h at RT. The solvent was evaporated and DMF (30 ml) was added and evaporated. DCM (25 ml) and EDCI (613 mg, 3.2 mmol) were added and the mixture stirred at RT for 4 h. Water (20 ml) was added and the layers separated. The aqueous layer was extracted with DCM (3×15 ml). The organic layer was washed with water (2×40 ml) and brine (2×40 ml), dried (MgSO$_4$) and concentrated. The crude solid was purified by column chromatography (SiO$_2$, EtOAc) to give the title product (400 mg, 1.05 mmol, 59%) as a white solid. $\delta_H$ (400 MHz, CDCl$_3$) 1.34-1.49 (4H, m), 1.70 (2H, quintet, J 7), 2.44 (2H, t, J 7), 2.55 (2H, t, J 7), 2.79 (4H, br. s), 3.18 (2H, q, J 6.2), 3.76 (2H, t, J 7.1), 5.87 (1H, br. s), 6.62 (2H, s); LCMS (ESI+) 380 (M+H)+, ret time 2.56 mins.

Intermediate 8

N-α-[S-Acetylthiopropionyl] lysine lysine lysine (ATP-KKK-OH)

H$_2$N-[Lys(Boc)]$_3$-Wang Resin (300 mg) was prepared from Fmoc-Lys(Boc) Wang Resin (0.53 mMol/g substitution) using standard Fmoc chemistry with 20% piperidine DMF for the Fmoc deprotection steps and a three fold excess of the Fmoc amino acid (Fmoc-Lys[Boc]OH) (0.52 mMol, 227 mg), TBTU (0.52 mMol, 163 mg), HOBT, (0.52 mMol, 70.2 mg) and DIPEA (0.7 mMol, 90.3 mg) in DMF (15 mL) for each of the coupling steps. N-succinimidyl S-acetylthiopropionate (0.2 mMol, 50 mg) in DMF (2.5 mL) was added and the reaction was shaken for 2 hours (ninhydrin negative). The resin was filtered, washed with DMF, DCM and dried with diethyl ether. The peptide was cleaved from the resin by shaking with 95% TFA/water for 2 hours, the resin removed by filtration and the solvent removed by evaporation. The residue was isolated by trituration with diethyl ether and purified by preparative RP-hplc (C-18 Vydac 5 µm particle size, 280 mm×25 mm column; gradient elution over 40 min, 0-40% acetonitrile/water/0.1% TFA; 20 mL/min) to give the title compound, 70 mg, 75%, after lyophilisation. ESMS 533 [M+1]; RP-hplc retention time 10.99 mins (C-18 Hichrome, 5 µm particle size, 250 mm×6 mm column 10-90% acetonitrile/water/0.1% TFA over 20 mins; 1 mL/min).

EXAMPLE 1

S-[3-({2-(3-{[3-(2,5-Dioxo-2,5-dihydro-1H-pyrrol-1-yl)propanoyl]amino}propoxy)-1,1-bis [(3-{[3-(2,5-dioxo-2,5-dihydro-1H-pyrrol-1-yl)propanoyl]amino}propoxy)methyl]ethyl}amino)-3-oxopropyl]ethanethioate

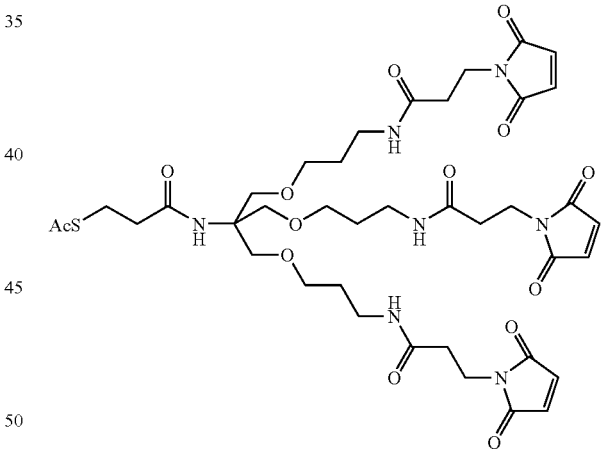

N-Maleimidopropionic acid NHS ester (230 mg, 0.87 mmol) and NEt$_3$ (0.17 ml, 1.24 mmol) were added to a solution of the product of intermediate 6 (100 mg, 0.25 mmol) in dimethylformamide (3 ml). The resulting mixture was stirred for 1.25 h at RT. Water (3 ml) and dichloromethane (3 ml) were added, and the layers separated. The aqueous layer was extracted with dichloromethane (3×3 ml). The organic layer was washed with water (3×10 ml), dried (MgSO$_4$) and concentrated. The crude oil was purified by column chromatography (SiO$_2$, EtOAc/hexane 1:1 then EtOAc then EtOAc/MeOH 20%) to give the title product (95 mg, 0.11 mmol, 44%) as a light yellow solid. $\delta_H$ (400 MHz, CD$_3$OD) 1.73 (6H, quintet, J 6.24), 2.32 (3H, s), 2.48 (6H, t, J 7.0), 2.54 (2H, t, J 7.0), 3.09 (2H, t, J 7.0), 3.23 (6H, t, J 5.8), 3.46 (6H, t, J 5.9), 3.69 (6H, s), 3.79 (6H, t, J 6.9), 6.84 (6H, s), 7.34 (1H, br. s), 7.95 (3H, br. s); TLC (EtOAc/MeOH 20%) rf 0.23; LCMS (ESI+) 876 M+, 877 (M+H)+, 878 (M+2H)+, ret time 2.63 mins.

EXAMPLE 2

S-[21-(2,5-Dioxo-2,5-dihydro-1H-pyrrol-1-yl)-5,5-bis({3-[(6-{[3-(2,5-dioxo-2,5-dihydro-1H-pyrrol-1-yl)propanoyl]amino}hexanoyl)amino]propoxy}methyl)-3,12,19-trioxo-7-oxa-4,11,18-triazahenicos-1-yl]ethanethioate

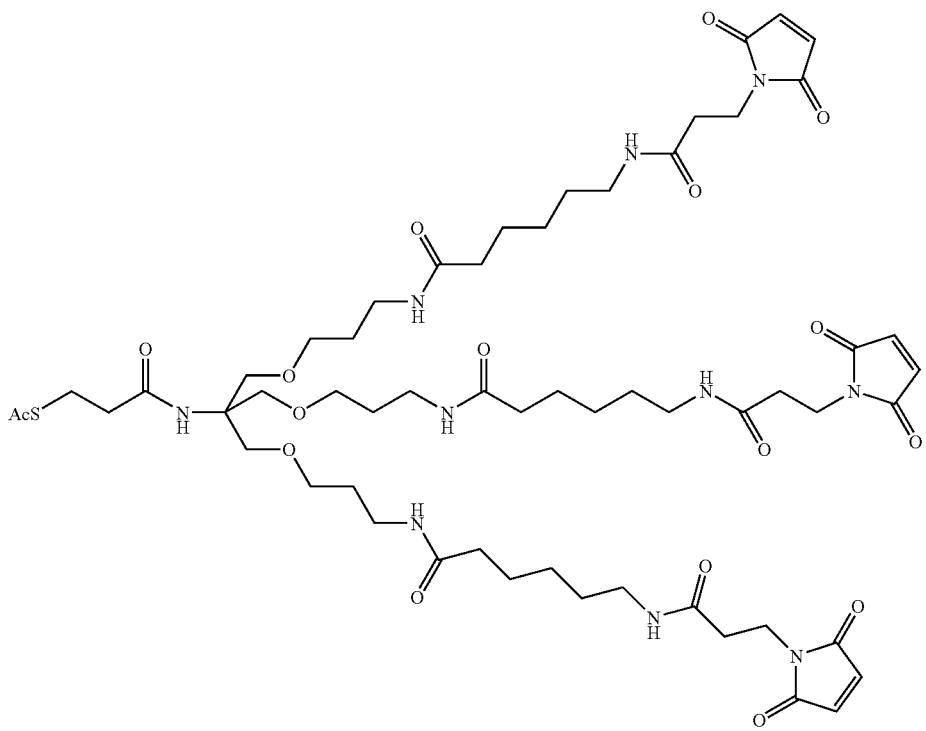

The compound of intermediate 7 (78.5 mg, 0.207 mmol) and NEt$_3$ (0.07 ml, 0.483 mmol) were added to a solution of the compound of intermediate 6 (53 mg, 0.069 mmol) in DMF (3 ml). The mixture was stirred for 2.5 h at RT and evaporated. Water (3 ml) and DCMe (3 ml) were added. The aqueous layer was extracted with DCM (3×3 ml). The organic layer was washed with water (3×10 ml), dried (MgSO$_4$) and concentrated. The residue was passed through a plug of silica gel (EtOAc then EtOAc/MeOH 1:1) to give a first batch of title product. The aqueous layer was back extracted with DCM (3×7 ml). This organic layer was dried (MgSO$_4$), concentrated, diluted with DCM (2 ml) and methanol (1 ml), treated with PS-TsCl (HL) resin (2.40 mmol/g, 300 mg) for 3 h, filtered and evaporated to give a second batch of title product. The two batches were combined to give the title product (11 mg, 0.01 mmol, 13%) as a white solid. $\delta_H$ (400 MHz, CD$_3$OD) 1.19-1.25 (6H, m), 1.38 (6H, quintet, J 7.2), 1.55 (6H, quintet, J 7.6), 1.64 (6H, quintet, J 6.4), 2.08 (6H, t, J 7.4), 2.20 (3H, s), 2.35 (6H, t, J 6.9), 3.01 (6H, t, J 6.9), 3.15 (6H, t, J 6.9), 3.37 (6H, t, 5.9), 3.58 (6H, s), 3.66 (6H, t, J 6.9), 6.71 (6H, s); LCMS (ESI+) 1215 M$^+$, ret time 2.63 mins.

EXAMPLE 3

S-[30-(2,5-Dioxo-2,5-dihydro-1H-pyrrol-1-yl)-5,5-bis[25-(2,5-dioxo-2,5-dihydro-1H-pyrrol-1-yl)-7,23-dioxo-2,10,13,16,19-pentaoxa-6-22-diazapentacos-1-yl]-3,12,28-trioxo-7,15,18,21,24-pentaoxa-4,11,27-triazatriacont-1-yl]}ethanethioate

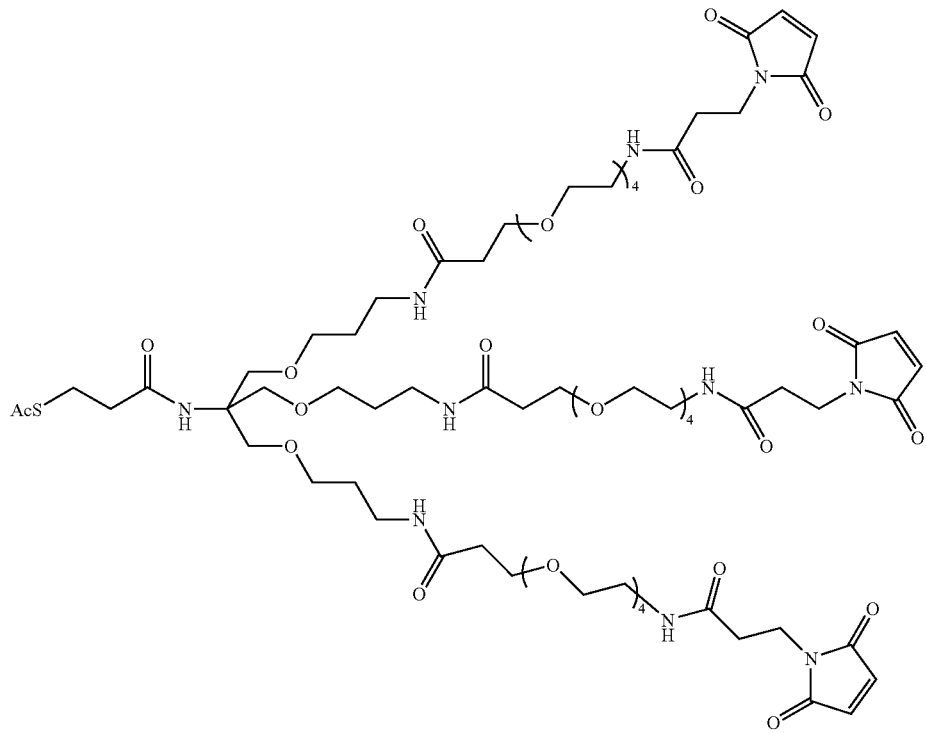

Mal-d-PEG$_4$-NHS ester (Quanta Biodesign, USA) (100 mg, 0.194 mmol) and NEt$_3$ (0.07 ml, 0.483 mmol) were added to a solution of the compound of intermediate 6 (52 mg, 0.065 mmol) in DMF (3 ml). The mixture was stirred for 2 h at RT and evaporated. Aq HCl (0.1M, 8 ml) and DCM (7 ml) were added. The organic layer was washed with aq HCl (0.1M, 3×8 ml), dried (MgSO$_4$) and concentrated. The residue was dissolved in DCM (5 ml) and washed with aq HCl (0.1M, 3×5 ml). The aqueous layers of the two first washes were combined and extracted with DCM (2×5 ml). The organic extracts were combined, dried (MgSO$_4$) and concentrated to give the title product (10 mg, 0.006 mmol, 9%) as a colourless oil. $\delta_H$ (400 MHz, CDCl$_3$) 2.24 (3H, s), 2.38 (6H, t, J 6.1), 2.45 (6H, t, J 7.3), 2.51-2.56 (2H, m), 3.01 (6H, t, J 7.1), 3.23 (6H, q, J 6.4), 3.34 (6H, t, J 5.3), 3.39 (6H, m), 3.47 (6H, t, J 9.3), 3.54-3.58 (42H, m), 3.60 (6H, s), 3.67 (6H, t, J 2.88), 3.77 (6H, t, J 6.8), 6.53 (1H, s), 6.63 (6H, s), 6.70-6.73 (6H, br. s); LCMS (ESI+) 809 M$^{2+}$, 540 M$^{3+}$, ret time 2.43 mins.

EXAMPLE 4

S-{3-[(2-[3-(2,5-Dioxo-2,5-dihydro-1H-pyrrol-1-yl)propoxy]-1,1-bis{[3-(2,5-dioxo-2,5-dihydro-1H-pyrrol-1-yl)propoxy]methyl}ethyl)amino]-3-oxopropyl}ethanethioate

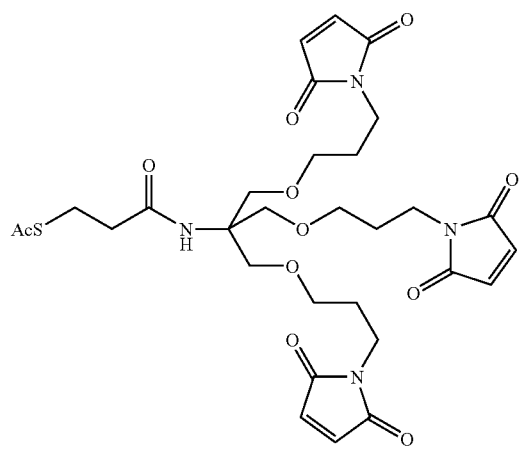

The compound of intermediate 6 (84 mg, 0.11 mmol) was dissolved in aq sodium hydrogen carbonate (1M, 2 ml). N-methoxycarbonyl maleimide (102 mg, 0.66 mmol) was added at 0° C. The mixture stirred for 5 min, diluted with water (1 ml) and acetonitrile (3 ml), and stirred at RT for no longer than 30 min. DCM (10 ml) was added. The aqueous layer was extracted with DCM (3×6 ml). The combined organic layers were washed with aq HCl (0.1M, 3×15 ml), dried (MgSO$_4$) and concentrated. The crude oil was purified by column chromatography (SiO$_2$, EtOAc/hexane 1:1) to give the title product (10 mg, 0.01 mmol, 14%) as a colourless oil. δ$_H$ (400 MHz, CDCl$_3$) 1.77 (6H, quintet, J 6.4), 2.23 (3H, s), 2.50 (2H, t, J 6.9), 3.05 (2H, t, J 6.9), 3.33 (6H, t, J 5.9), 3.56 (6H, t, J 6.8), 3.62 (6H, s), 6.33 (1H, s), 6.63 (6H, s); LCMS (ESI+) 663 M$^+$, ret time 3.26 mins.

EXAMPLE 5

N-α-[S-Acetylthiopropionyl]-tris N-[ε-maleimidocaproyloxy]lysine lysine lysine (ATP-(K-[EMC])$_3$—OH)

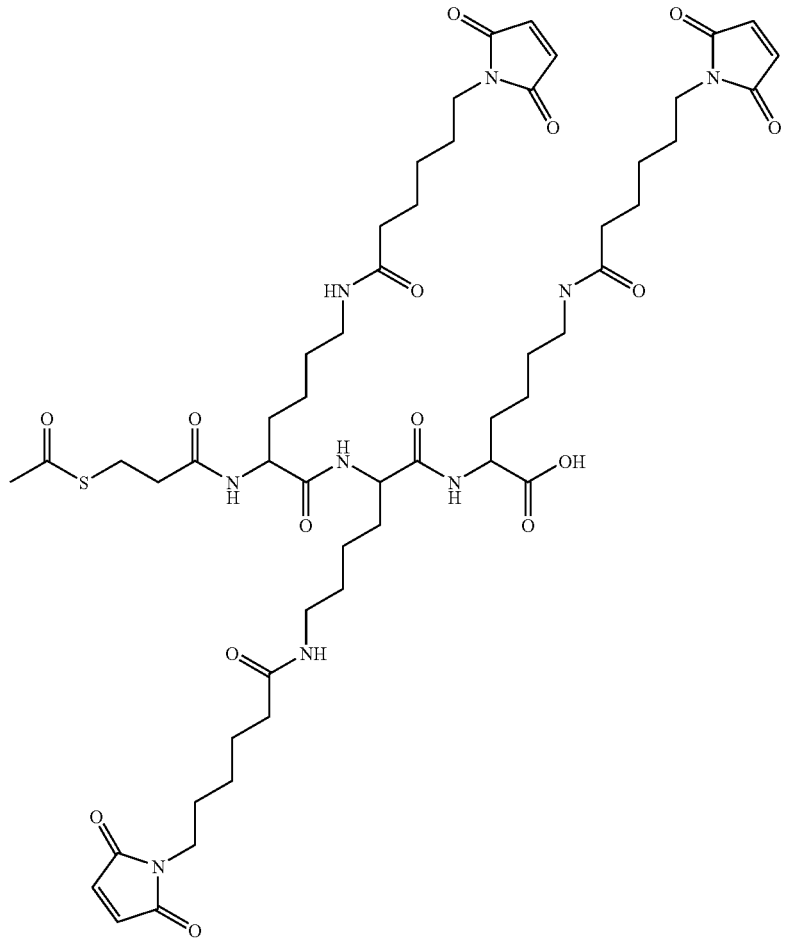

The compound of intermediate 8, (70 mg, 0.13 mMol), N-[ε-maleimidocaproyloxy]succinimide ester (25 mg, 0.08 mMol) and DIPEA (15 mg, 0.12 mMol) was dissolved in DMSO (2 mL) and stirred for 2 hours. At this more N-[ε-maleimidocaproyloxy]succinimide ester (25 mg, 0.08 mMol) and DIPEA (15 mg, 0.12 mMol) was added and the reaction stirred for a further 1 hour. The solution was diluted with water (10 mL) and the mixture purified by RP-hplc hplc (C-18 Vydac 5 μm particle size, 280 mm×25 mm column; gradient elution over 40 min, 20-60% acetonitrile/water/0.1% TFA; 20 mL/min) to give the title compound, 50 mg, 35%, after lyophilisation. ESMS 1112 [M+1]; RP-hplc retention time 18.7 mins (C-18 Hichrome, 5 μm particle size, 250 mm×6 mm column 5-85% acetonitrile/water/0.1% TFA over 20 mins; 1 mL/min).

EXAMPLE 6

Conjugation of Antibodies to the Compounds of Examples 1-4

An engineered Fab' containing a single hinge thiol (see for example, U.S. Pat. No. 5,677,425; WO9825971) at 10 mg/ml in 50 mM sodium phosphate buffer, pH 6.0 (containing 2 mM EDTA) was selectively reduced with 2-mercaptoethylamine to a final concentration of 5 mM at 37° C. for 30 minutes. Excess reductant was removed by gel filtration and success of reduction was measured by titration of the generated thiol with 4,4'-dithiodipyridine. The linker (10 mM in DMF) was added to the reduced Fab' (4.9 mg/ml in 50 mM sodium acetate buffer, pH 6.0 containing 2 mM EDTA) in two separate aliquots over 20 minutes to result in a final molar ratio of 3.3:1 (Fab':linker). The reaction mix was maintained at 37° C. for 18 hours. The extent of the reaction was monitored by HPLC gel filtration (GF250:0.2M sodium phosphate buffer, pH 7.0, containing 10% ethanol) and cross linking confirmed by SDS PAGE (under both non-reducing and reducing conditions).

The reaction resulted in 33% tri-Fab'; 13% di-Fab' and 54% Fab'.

The resultant tri-Fab' was purified via cation exchange (SP-Separose HP) utilising a sodium chloride gradient in 50 mM sodium acetate, pH 4.50, and characterised by HPLC (gel filtration: GF250; eluted with 0.2M sodium phosphate, containing 10% ethanol) and SDS PAGE.

EXAMPLE 7

Conjugation of Antibodies to the Compound of Example 5

An engineered Fab' with a single hinge thiol, at 10 mg/ml in 50 mM sodium phosphate buffer, pH 6.0 (containing 2 mM EDTA) was selectively reduced with 2-mercaptoethylamine to a final concentration of 5 mM at 37° C. for 30 minutes. Excess reductant was removed by gel filtration and success of reduction was measured by titration of the generated thiol with 4,4'-dithiodipyridine.

The linker (2 mM in DMF) was added to the reduced Fab' (5.50 mg/ml in 50 mM sodium acetate buffer, pH 6.0 containing 2 mM EDTA) in two separate aliquots over 20 minutes to result in a final molar ratio of 3.3:1 (Fab':linker). The reaction mix was maintained at 37° C. for 18 hours. The extent of the reaction was monitored by HPLC gel filtration (GF250:0.2M sodium phosphate, pH 7.0 containing 10% ethanol) and cross linking confirmed by SDS PAGE (under both non-reducing and reducing conditions). The reaction resulted in 53% tri-Fab', 13% di-Fab; and 34% Fab' as judged by HPLC gel filtration.

The resultant tri-Fab' molecule was purified by cation exchange: SP-Sepharose HP. The di-Fab' and Fab' were eluted in 50 mM sodium acetate buffer, pH 4.50 containing 125 mM sodium chloride and the tri-Fab' was eluted in 50 mM sodium acetate, pH 4.50 using a sodium chloride gradient of 125 mM to 250 mM over 20 column volumes.

EXAMPLE 8

Attachment of PEG to the Tri-Fab of Examples 6 and 7

Purified tri-Fab' prepared as above was buffer exchanged into 0.1M sodium phosphate buffer, pH 7.50, containing 2 mM EDTA and then incubated with hydroxylamine hydrochloride (final concentration of 50 mM) for 2 hours at ambient temperature. The success of the deprotection reaction to liberate a thiol group was measured by titration with 4,4'-dithiodipyridine: pre deprotection mix resulted in 0.26 thiols per tri-Fab', whereas post deprotection mix gave 1.10 thiols per tri-Fab'.

Deprotected tri-Fab' in 0.1M sodium phosphate, pH 7.50 (containing 50 mM hydroxylamine hydrochloride and 2 mM EDTA) was incubated with a three times molar excess of mono-maleimide derivatives of PEG (5-49K) at room temperature for 18 hours. The extent of reaction was analysed by HPLC gel filtration (GF250: 0.2M sodium phosphate, pH 7.0, containing 10% ethanol) and SDS PAGE (under non-reducing and reducing conditions). The reaction resulted in >80% of PEGylated products as judged by HPLC gel filtration. Non-PEGylated tri-Fab' was removed by application of the reaction mix to gel filtration S-300HR (primed with 1% PEG$_{20K}$) or cation exchange SP-Sepharose HP and the resultant PEGylated product characterized by HPLC gel filtration and SDS PAGE as before.

EXAMPLE 9

Attachment of a Fluorescent Dye to the Tri-Fab' of Examples 6 and 7

Deprotected tri-Fab' was prepared as described in Example 8. Deprotected tri-Fab' in 0.1M sodium phosphate, pH 7.50 (containing 50 mM hydroxylamine hydrochloride and 2 mM EDTA) was incubated with a six times molar excess of Alexa Fluor® 488 C$_5$ maleimide (Molecular Probes A-10254) for 18 hours at room temperature. The excess reagent was removed by gel filtration. The degree of labelling was calculated using the protein and dye concentrations with the appropriate molar extinction coefficients at the absorption maxima to result in 1.11 dyes per TFM molecule.

The invention claimed is:
1. A compound of formula (I):

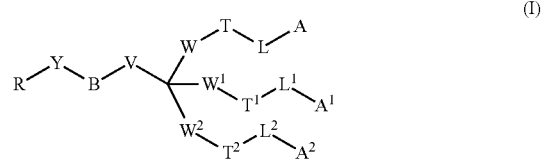

wherein:
A, A$^1$ and A$^2$ independently represent an antibody or fragment thereof;
L, L$^1$ and L$^2$ independently represent a spacer group;
R represents a reactive group which is suitable for attaching an effector molecule but does not react with any of A, A$^1$ and A$^2$, and wherein R is selected from

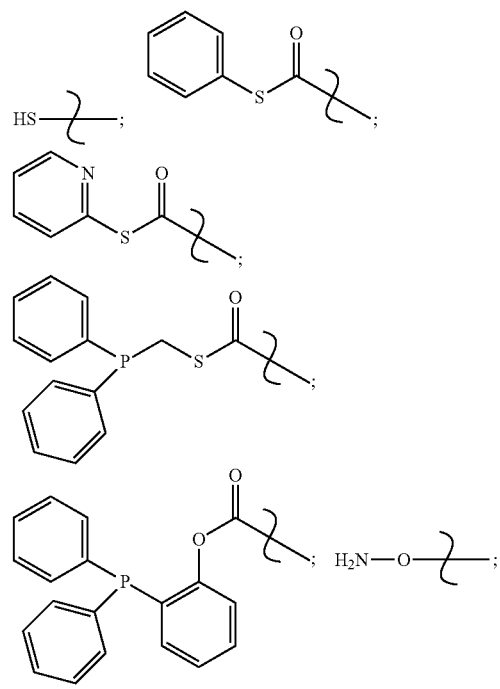

-continued

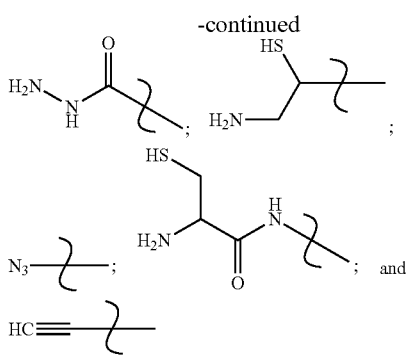

except that when Y represents a covalent bond and B represents —NHCO— or —CO— then R is selected from

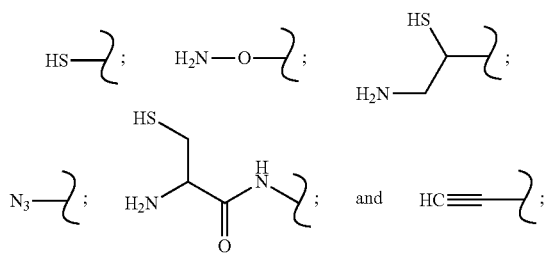

Y represents a covalent bond or —(CH$_2$)$_y$-;
B represents —CONH—, —NHCO— or —CO—;
V represents a covalent bond or —(CH$_2$)$_v$-;
W, W$^1$ and W$^2$ independently represent —(CH$_2$)$_w$O—;
T, T$^1$ and T$^2$ independently represent a linker group;
v is 1, 2, 3 or 4;
w is 1, 2, 3 or 4; and
y is 1, 2, 3, 4, 5 or 6.

2. The compound according to claim 1 wherein A, A$^1$ and A$^2$ are each an Fab' fragment.

3. The compound according to claim 1 wherein L, L$^1$ and L$^2$ are succinimide.

4. The compound according to claim 1 wherein T, T$^1$ and T$^2$ are independently selected from —(CH$_2$)$_t$-, —(CH$_2$)$_t$NHCO(CH$_2$)$_n$-, —(CH$_2$)$_t$NHCO(CH$_2$)$_x$NHCO(CH$_2$)$_n$-, —(CH$_2$)$_t$NHCO(CH$_2$)$_p$(OCH$_2$CH$_2$)$_z$NHCO(CH$_2$)$_n$-, —(CH$_2$)$_r$NHCO(CH$_2$)$_m$-,

wherein:
t is 1, 2, 3, 4, 5, 6, 7, 8, 9 or 10;
n is 1, 2, 3, 4, 5 or 6;
x is 2, 3, 4, 5 or 6;
z is 1 to 500;
p is 1, 2, 3, 4, 5 or 6;
m is 1, 2, 3, 4, 5 or 6; and
r is 2, 3, 4 or 5.

* * * * *